United States Patent [19]
Chaikof et al.

[11] Patent Number: 5,741,325
[45] Date of Patent: Apr. 21, 1998

[54] SELF-EXPANDING INTRALUMINAL COMPOSITE PROSTHESIS

[75] Inventors: Elliot L. Chaikof, Dunwoody; Peter J. Ludovice, Atlanta, both of Ga.

[73] Assignees: Emory University; Georgia Tech Research Corp., both of Atlanta, Ga.

[21] Appl. No.: 657,975

[22] Filed: May 3, 1996

Related U.S. Application Data

[63] Continuation of Ser. No. 131,156, Oct. 1, 1993, abandoned.
[51] Int. Cl.⁶ .................... A61F 2/06; A61F 2/04
[52] U.S. Cl. .................... 623/1; 623/12
[58] Field of Search .................... 623/1, 11, 12; 606/194, 195, 198, 191, 193, 152, 153, 155, 158; 600/36

[56] References Cited

U.S. PATENT DOCUMENTS 4,994,701  2/1991  MacGregor .................... 606/194
5,366,504  11/1994  Andersen et al. .................... 623/11

FOREIGN PATENT DOCUMENTS 1205743  9/1970  United Kingdom .................... 623/1

*Primary Examiner*—Debra S. Brittingham
*Attorney, Agent, or Firm*—Needle & Rosenberg, P.C.

[57] ABSTRACT

This invention relates to a self-expanding intraluminal composite prosthesis comprised of a rigid reinforcing component and sealing component. The prosthesis may be fabricated as either a straight or bifurcated tubular structure and is applicable to the treatment of any bodily passage including, but not limited to, vascular applications, e.g., aneurysms, arteriovenous fistulas, as well as stenotic regions of the peripheral circulation which have been percutaneously dilated but are at high risk for restenosis. The major attributes of this prosthesis can include the use of a unique multilayered biaxial braid which thereby creates a homogeneously blended composite with isotropic deformation and expansion characteristics and an associated high contraction ratio. The use of multiple layers allows for the fabrication of a device of varied porosity while retaining adequate tensile or mechanical wall strength.

22 Claims, 2 Drawing Sheets

SELF-EXPANDING INTRALUMINAL COMPOSITE PROSTHESIS

This application is a continuation of application Ser. No. 08/131,156, filed Oct. 1, 1993 which status is abandoned.

BACKGROUND OF THE INVENTION

1. Field of the Invention

This invention relates to intraluminal prosthetic devices. In particular, this invention relates to self-expanding intraluminal composite prosthetic devices for use, e.g., in endovascular applications.

2. Background Art

Since 1975, vascular prostheses composed of either knitted or woven Dacron® fibers or expanded PTFE (Gore-Tex®) have been established standards in anastomotic surgical arterial reconstruction. In the past decade, however, a steady growth of non-surgical transcatheter techniques and related devices have broadened both potential applications and overall suitability of endovascular reconstruction. In particular, angioplasty with or without endovascular stent placement has become an accepted adjunct in the management of atherosclerotic occlusive disease.

In the past, aneurysmal aortic disease has been treated almost exclusively by resection and surgical graft placement. Recently, however, successful preliminary tests have been reported for transfemoral endovascular grafting as an alternative therapeutic option. In contrast to standard surgical repair, the use of an endovascular device does not entail the removal of the diseased aorta, but serves to create a conduit for blood flow in the event of subsequent aneurysm rupture. It has been postulated that an endovascular graft may, as a secondary effect, lower the rate of aneurysm expansion and late rupture via a reduction of hemodynamically induced wall stresses. Endovascular aortic prostheses under current commercial development consist almost exclusively of grafts and stents attached together to form a single device. The stent secures the graft in a desired position and reduces the risk of late prosthetic migration.

There are presently two classes of stents in widespread clinical use categorized with respect to their mode of expansion: balloon expandable and self expanding. Balloon expandable stents typically consist of slotted or wire mesh tubes that can be permanently expanded after operator controlled balloon inflation. At least four U.S. patents have been granted (see, Palmaz: U.S. Pat. Nos. 4,739,762; 4,739,762; 4,776,337; and 5,102,417 and Strecker, E. P.; Liermann, D.; Barth, K. H.; Wolf, H. R. D.; Freudenberg, N.; Berg, G.; Westphal, M.; Tsikuras, P.; Savin, M.; and Schneider, B., Radiology, 175, 97-102 (1990)). Characteristically, self-expanding stents are loose wire meshes that can be compressed inside a sheath which, when removed, allows the stent to expand without the use of an inflating balloon. Many models are in common use including the MEDINVENT® stents, (see, Jedwab, M. R. and Clerc, C. O. J. Appl. Biomater, 4, 77-85 (1993) and Gianturco, Yoshioka, T.; Wright, K.; Wallace, S.; Lawrence Jr., D. D.; Gianturco, C. Amer. J. Radiology, 151, 673-676 (1988)).

Recently, Nitinol has been suggested as an alternative to stainless steel which has been the standard stent fabrication material (see, Balko, A.; Piasecki, G. J.; Shah, D. M.; Carney, W. I.; Hopkins, R. W. and Jackson, B. T., J. Surg. Res., 40, 305-309 (1986)). This nickel titanium alloy, also called "memory metal", will assume its original annealed shape when heated above a particular temperature. The ability to produce devices of smaller cross-sectional area (flow profile) is its major advantage. Nonetheless, it has two major disadvantages. Nitinol requires irrigation with cold saline solution during placement to prevent premature expansion. Additionally, its anisotropic expansion may cause damage to the vascular wall.

Most stent delivery systems are based on multi-sheath catheters. Self-expanding stents are deployed when the outer sheath of the catheter is retracted. The stent expands and the catheter is withdrawn. Balloon expandable stents are seated on an angioplasty balloon. After the sheath is removed, the balloon is inflated to deploy the stent. Catheter delivery systems have only recently been used to deploy grafts, but follow the same principles outlined above.

Commercially available vascular grafts for surgical applications are typically composed of polyethyleneterepthalate (DACRON®) fibers or extruded polytetrafluoroethylene (GORE-TEX®). Woven and knitted grafts are crimped in an accordion-like fashion along their circumference to prevent "kinking" when traversing curves or bends. Mechanistically, crimping allows the graft to expand longitudinally but limits radial contraction. Weave patterns and their associated porosity and handling characteristics for sutured anastomoses remains the major difference among graft types (see, Dumicans, U.S. Pat. No. 4,923,470; and Kaster, U.S. Pat. No. 4,441,215). Such devices are not suitable for endovascular applications although woven and knitted DACRON® grafts have been tried for endovascular grafting. Crimping appears necessary to reduce kinking but limits the compressibility and cross-sectional flow profile of the device.

The incorporation or "healing" of a fabric-based vascular prosthesis may depend, in part, on an optimal porosity of the prosthesis (see, Snyder, R. W. and Botzko, K. M. from Biologic and Synthetic Vascular Prosthesis, edited by J. C. Stanley, Grune and Stratton: New York, (1982), pp. 485-494; and Turner, R. J., Hoffman, H. L., Weinburg, S. L. from Biologic and Synthetic Vascular Prostheses, edited by J. C. Stanley, Grune and Stratton: New York, (1982), pp. 509-522). Wesolowski and co-workers reported that increased porosity was associated with a reduction in graft calcification (Wesolowski, S. A., Liebig, W. J., Karlson, K. E., et al., Surgery, 50, 91-100 (1961)). As an outgrowth of this work, the vascular graft industry pursued, for a time, the goal of an ultrathin, highly porous graft. This approach was abandoned after mechanical failure plagued these grafts (see, Ottinger, L. W. Darling, R. C. Werthlin, L. S., et al., Arch. Surg. 111, 146-149 (1976)).

Sutureless grafts for vascular reconstruction were reported and patented as early as the 1960's as an alternative to standard operative aortic repair. In the 1980's, percutaneous transcatheter techniques grew in popularity and the concept of sutureless grafting was reintroduced as an endovascular approach to occlusive and aneurysmal disease. A triple layered air-inflatable graft has been patented, but the potential for failure appears substantial because of the complex arrangement of membranes, valves, and seals (Pigott, U.S. Pat. No. 5,156,620). Sutureless endovascular prostheses have otherwise included: (i) graft/staple; (ii) graft/hook; and (iii) graft/stent combinations.

Graft/staple combinations are covered by two U.S. patents in which a balloon catheter system delivers a standard vascular graft with staples lodged in the end of the graft (Lazaras, U.S. Pat. Nos. 4,787,899 and 5,104,399). The inflation of the balloon implants the staples into the vascular wall, thereby securing the graft. Two additional patents exist for graft/hook combinations (Kornberg, U.S. Pat. Nos.

4,562,596 and 4,617,932). Angled hooks on the proximal portion of the graft secure it in place. These grafts may be expanded either mechanically or with the use of flexible self-expanding rings.

Currently, most approaches follow the graft/stent concept and can be further classified as: (i) fabric or membrane covered stents; (ii) grafts bridged by stents (Rhodes, U.S. Pat. No. 5,122,154); and (iii) stents bridged by a graft. Most commercial efforts have focused on the latter of these three approaches. Based on earlier work by Parodi, Johnson & Johnson is developing a prosthesis comprised of a woven DACRON® tube graft connected to a balloon expandable Palmaz-type stent. The Cook Corp. is investigating the use of self-expanding Gianturco stents in association with a bifurcated graft. This is an extension of studies performed by Green. Endovascular Technologies (EVT) of California has placed a hook containing self-expanding ring at the proximal end of a vascular graft. This prosthesis is essentially a combination of the Rhodes and Kornberg inventions. Finally, the Meditech Corporation is evaluating a fabric covered balloon expandable Strecker stent. The stent consists of interlocked tantalum wires.

However, these devices may experience mechanical failure due to stress concentration at the point of attachment or due to the lack of mechanical stability along the long axis of the graft portion of the device. Therefore, there still exists a need for an endovascular graft that provides optimal porosity yet retains mechanical integrity.

SUMMARY OF THE INVENTION

It is an object of the present invention to provide a superior intraluminal prosthetic device which has the following qualifies:

1. A device that can be easily transported in any body passage, e.g., to an aneurysm (or region of arterial disease or injury) via endovascular means so as to avoid invasive surgical techniques.
2. A device that can be easily deployed without damaging vascular tissue.
3. A device that easily fits into curved blood vessels, while retaining sufficient mechanical integrity to contain pulsatile blood flow.
4. A device that minimizes the concentration of stress which can lead to mechanical failure.
5. A device that is able to treat arterial malfunctions in the vicinity of arterial or aortic branches.
6. A device that is designed to treat aneurysms or arterial disease in the vicinity of bifurcated blood vessels.

The present invention overcomes the deficiencies of the prior art by providing a porous, self-expanding intraluminal composite prosthesis comprised of a rigid reinforcing component and sealing component. The prosthesis may be fabricated as either a straight or bifurcated tubular structure and is applicable to the treatment of any bodily passage including, but not limited to, vascular applications, e.g., aneurysms, arteriovenous fistulas, as well as stenotic regions of the peripheral circulation which have been percutaneously dilated but are at high risk for restenosis. The major attributes of this prosthesis can include the use of a unique multilayered biaxial braid which thereby creates a homogeneously blended composite with isotropic deformation and expansion characteristics and an associated high contraction ratio.

The composite layered design of the present invention also satisfies a need in the art by providing a prosthesis with optimal porosity and mechanical stability by blending a reinforcing component with the sealing components typically used in vascular grafts. In one embodiment, the use of multiple layers allows for the fabrication of a device of varied porosity while retaining adequate tensile or mechanical wall strength. By increasing the number of layers, the porosity can be reduced for high risk or heparin treated patients.

Specifically, the present invention provides a self-expanding intraluminal composite prosthesis, comprising an elongated tubular shaped member having a body portion that is formed by at least one layer of a composite material comprised of a plurality of strands of a reinforcing fiber and a plurality of strands of a sealing fiber. The fibers comprising the body portion can be interwoven, e.g., in a unique biaxially braided design. The tubular shaped member has an expanded diameter, a radially contracted diameter, and an operable diameter which is intermediate the expanded and radially contracted diameters. The tubular shaped member can be compressed radially along its longitudinal axis to permit intraluminal delivery of the tubular shaped member through a body passage to a predetermined delivery site wherein the tubular shaped member self-expands upon deployment within the body passage to its operable diameter. The reinforcing fiber can be comprised of a material selected from the group consisting of biocompatable metals, polymers, and organic fibers. The sealing material can be any biocompatable polymer including, but not limited to, polyethyleneterepthalate, polytetrafluoroethylene, polysiloxane, and nylon or any biocompatable carbon fibers.

In one embodiment, the invention provides a self-expanding intraluminal composite prosthesis wherein the tubular shaped member further comprises a first end portion and an opposing second end portion with the body portion interconnecting the end portions. At least one of the end portions has an expanded resting diameter that is larger than the expanded resting diameter of the body portion such that the larger diameter end portion exerts a force upon the luminal surface of the body passage sufficient to anchor the tubular shaped member at a predetermined delivery site. The end portions can be formed from a single layer of the biaxially braided interwoven reinforcing and sealing fibers or, alternatively, from a single layer of a biaxially braided interwoven reinforcing fiber.

In another embodiment, one end portion contains a segment which is sufficiently porous such that placement of the segment at the intersection of a branch in the body passage allows bodily fluids to pass through the segment and into the branches of the body passage, thereby maintaining fluid communication between the body passage and the branch.

In a further embodiment, the invention provides a self-expanding intraluminal composite prosthesis that is suitable for placement in a bifurcated body passage. The body portion of the prosthesis is bifurcated forming two branches having expanded diameters that are less than the expanded diameter of the body portion proximal to the bifurcation.

In a preferred embodiment, the present invention provides a self-expanding intraluminal composite prosthesis specifically designed for endovascular applications.

The present invention also provides a method for treating aortic aneurysmal disease. Also provided is the device of the present invention mounted on a delivery catheter within a removable sheath located on the catheter.

DETAILED DESCRIPTION OF THE INVENTION

The present invention may be understood more readily by reference to the following detailed description of specific embodiments and the Examples and Figures included therein.

As used in the claims, "a" means one or more.

The present invention provides a true composite device that possesses the structural and mechanical reinforcing characteristics of a stent with the containment characteristics of a graft. A "composite" as used herein refers to two components, e.g., the reinforcing and sealing components that are blended rather than two devices that are attached. Blending of components can be achieved by any of a number of means including, but not limited to, interweaving the component fibers to form a composite structure.

The device of the present invention consists of a mechanically stiff component that is blended with a more compliant component, the combination of which is fabricated as a straight or branched tubular structure. The stiff component provides mechanical resistance such that any radial deformation of the tube requires some force. Further, the elastic deformation characteristics of the two components can be identical such that deformation of the device (for delivery or deployment) occurs in an isotropic fashion so as to avoid internal stress gradients that may cause the two components to separate. The composite nature of the device homogeneously distributes these forces so as to minimize the possibility of device failure. This is in contrast to the assembly of two separate devices (such as a graft and a stent) where the stress is concentrated in whatever means is used to fasten the two devices together. The isotropic expansion characteristics possessed by the present invention also minimize the damage to vascular tissue that potentially occurs with other devices such as a Nitinol stent.

Although braiding of the components comprises the preferred embodiment of the device, blending of any two components that possesses these consistent deformation characteristics may be used. Other possible composite systems include an expanding metal mesh protruded in a tubular form with a polymeric matrix that is subsequently cross-linked, by chemical, radiative or other means to form an elastomeric matrix with deformation characteristics consistent with those of the metal mesh.

Figure 4:
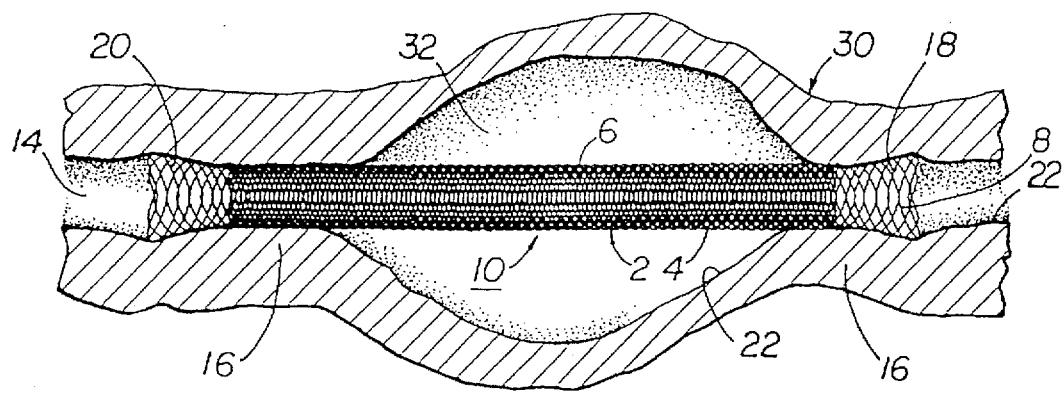
FIG. 4 is a side view of the prosthesis deployed within a vertical cross-section of in an aortic aneurysm.
Figure 5:
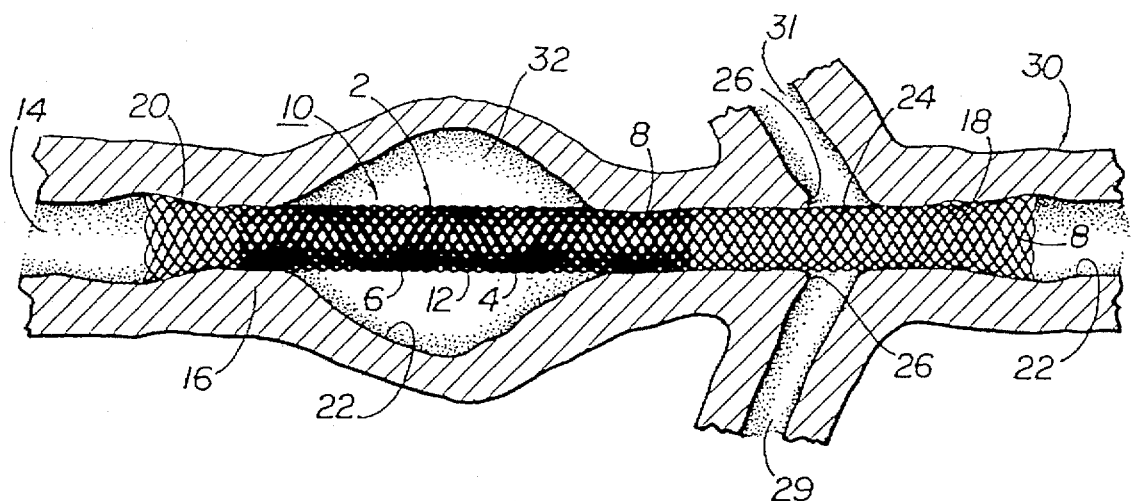
FIG. 5 is a side view of one embodiment of the prosthesis deployed within a vertical cross-section of an aneurysm and an aortic branch.

Referring now to the figures, the present invention provides a self-expanding intraluminal composite prosthesis 10, comprising an elongated tubular shaped member 2 having a body portion 4, the body portion 4 being formed by at least one layer of a composite material 6, the composite material 6 being comprised of a plurality of strands of a reinforcing fiber 8 and a plurality of strands of a sealing fiber 12. The fibers 8,12 are interwoven, thereby forming the composite material 6. The tubular shaped member 2 has an expanded or resting diameter, a radially contracted diameter, and an operable diameter when deployed in a body passage 14 which is intermediate the expanded and radially contracted diameters, the tubular shaped member 2 being radially compressible along its longitudinal axis between the expanded and radially contracted diameters to permit intraluminal delivery of the tubular shaped member 2 through a body passage 14 to a predetermined delivery site 16. At the predetermined delivery site 16, the tubular shaped member can self-expand within the body passage 14 to its operable diameter as shown in FIGS. 4–5.

Figure 1:
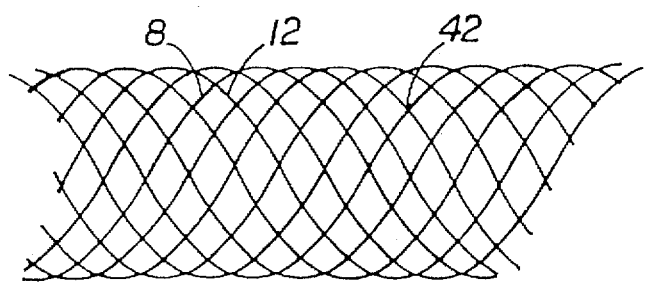
FIG. 1 is a side view of the interwoven fibers of a segment of the single layer of the body portion of the prosthesis.

In a preferred embodiment, the invention provides a self-expanding intraluminal composite prosthesis 10, wherein the composite material 6 is interwoven in a biaxially braided design as shown in FIG. 1. The biaxial braid (diamond braid) design is a one over one configuration. It is contemplated by the invention that other braids such as a regular two over two braid or a hercules three over three braid can be utilized.

The reinforcing fibers 8 can be comprised of any biocompatible material including, but not limited to, metals, polymers, organic fibers or combinations thereof. The sealing fibers 12 can be comprised of any biocompatable polymer or carbon fiber. Examples of suitable polymers include, polyethyleneterepthalate, polytetrafluoroethylene, polyurethane, polysiloxane or nylon.

Figure 2:
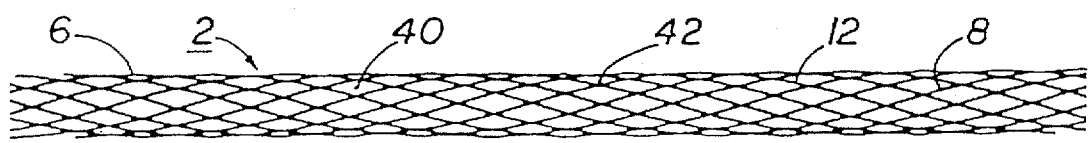
FIG. 2 is a side view of the prosthesis in radial compression.

Preferrably, the diameter of the fibers 8,12 is between about 0.1 mm and 0.5 mm. A single layer of the composite material 6, as shown in FIGS. 1–2, is normally porus and the pore size 40 is between about 0.5 mm and 2.5 mm. The pore size 40 in the biaxial braid design can be varied by adjusting the number of sealing fibers 12 per layer, the diameter of the reinforcing and sealing fibers 8,12, the distance between the fibers 8,12, and the angle formed where the fibers intersect each other at the point of interlock 42. The angle formed by the fibers 8, 12 at the point of interlock 42 can range between about 60° and 130°, but the preferred angle is about 90° when the tubular shaped member 2 is at its expanded (resting) diameter. The contraction ratio for the prosthesis of the present invention can range from between about 3 and 10. A presently preferred ratio is about 5.

In one embodiment, the self-expanding intraluminal composite prosthesis 10 of the invention is constructed from reinforcing and sealing fibers 8,12 that have substantially similar elastic deformation characteristics, thereby permitting isotropic deformation, e.g., radial compresion of the tubular shaped member 2 as shown in FIG. 2.

Figure 3:
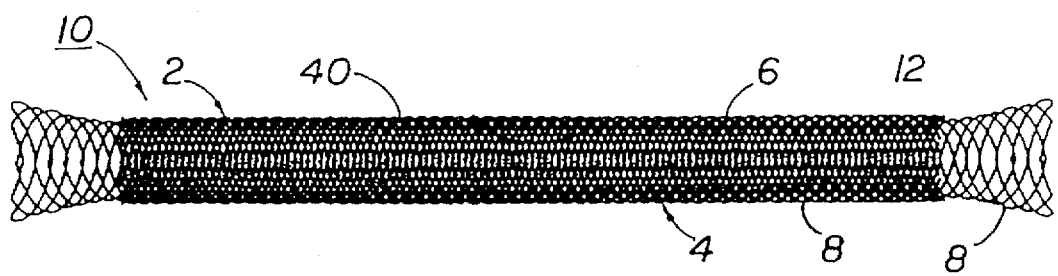
FIG. 3 is a side view of one embodiment of the invention.

As shown in FIGS. 3–6, the tubular shaped member 2 of the present invention can further comprise a first end portion 18 and an opposing second end portion 20 with the body portion 4 interconnecting the end portions 18,20. It is contemplated by the invention that at least one (or both) of the end portions 18,20 can have an expanded diameter that is larger than the expanded diameter of the body portion 4 and an operable diameter, such that the larger diameter end portion(s) 18,20 exerts a force upon the luminal surface 22 of the body passage 14 at its operable diameter sufficient to anchor the tubular shaped member 2 at the predetermined delivery site 16 as shown in FIGS. 4–5. The end portions 18,20 can be constructed from materials selected from the group consisting of a single layer of the composite material 6 or from a single layer of the interwoven reinforcing fiber 8. In a preferred embodiment, the invention provides at least one of the end portions 18,20 in an interwoven biaxially braided design as shown in FIG. 3.

Referring now to FIG. 5, the present invention also provides a self-expanding intraluminal composite prosthesis 10, wherein the first end portion 18 is longer than the second end portion 20 and at least a segment 24 of the first end portion 18 is sufficiently porus such that placement of the segment 24 at the intersection of a branch 26 in the body passage 14 allows bodily fluids to pass through the segment 24 and into the branches 29,31 of the body passage 14, thereby maintaining fluid communication between the body passage 14 and the branches 29,31.

The prosthesis provided by the present invention can be used in any hollow body passage including, but not limited to, arteries, veins, bile ducts, and the like. In a preferred embodiment, the prosthesis of the present invention is designed for endovascular applications as shown in FIGS. 4–5. In those figures, the prosthesis 10 is deployed in a blood vessel 30 at a predetermined delivery site 16 which is an aneurysm 32.

Figure 6:
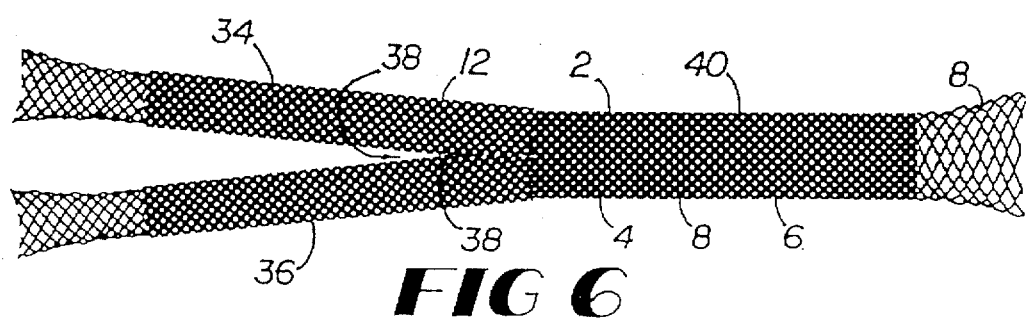
FIG. 6 is a top view of one embodiment of the prosthesis having a bifurcated body portion.

Referring now to FIG. 6, shown is an alternate embodiment of the self-expanding intraluminal composite prosthesis of the present invention wherein the body portion 4 is bifurcated along a part of its length forming two branches 34,36 such that the two branches 34,36 have an expanded diameter that is less than the expanded diameter of the body portion 4 proximal to the bifurcation 38. This embodiment forms a Y-shaped intraluminal prosthesis for placement in a bifurcated body passage (not shown).

The present invention also provides the self-expanding intraluminal composite prosthesis 10 mounted on a delivery catheter (not shown) within a removable sheath (not shown) located on the catheter. Also provided is a method for treating aortic aneurysmal disease comprising delivering the prosthesis provided by the present invention to a predetermined delivery site 16. Briefly, the prosthesis (mounted on a standard delivery catheter inside a sheath under radial compression) is inserted into the body passage and advanced along the passage to the predetermined delivery site 16. The prosthesis is deployed by retracting the sheath proximally along the long axis of the delivery catheter such that the prosthesis is uncovered. This removes the radially compressive forces exerted by the sheath and allows the prosthesis to self-expand to its operable diameter.

EXAMPLES

Referring again to FIG. 1, the preferred embodiment of the device is designed for endovascular applications and consists of a stiff reinforcing fiber 8, possibly of wire or a thermoplastic or thermoset polymer resin biaxially braided into a tubular structure with strands of a less stiff sealing fiber 12. Strands of the less stiff sealing fiber 12 form a sealed or semiporous structure to contain blood flow while the stiff reinforcing fiber provides structural reinforcement. These sealing strands can typically be made of synthetic or natural fiber that have been approved for devices such as DACRON®. A biaxially braided tubular structure can consist of an even number of filaments or strands wound in a helical fashion around a center longitudinal axis as seen in FIG. 1. Half of the strands (fibers 8,12) are wound in one direction, while the other half are wound in the other direction. The oppositely wound strands alternate passing over and under each other, each time their paths cross (the point of intersection 42) so as to form a mechanically stable intermeshed network. The body portion 4 can consist of multiple layers of the braided tube as shown in FIG. 1. These layers can be comprised of a minimum number of strands to provided mechanical stability (typically 8) up to whatever number is necessary to fabricate a tube of sufficient diameter for the particular body passage, e.g., a blood vessel. The layers may consist of sealing fibers 12, reinforcing fibers 8, or both of these components braided together. The biaxial braid shown in FIG. 1, typically called a diamond braid, comprises single oppositely wound strands crossing each other. The numbers of the strands that cross each other may be varied as long as all of the layers of the device contain a consistent braiding pattern.

The biaxial nature of the braid allows the device to be compressed significantly to be delivered endovascularly via a catheter type device. When compressed, the various layers of the device will appear as seen in FIG. 2. Other types of braids such as triaxial braids that contain reinforcing warp strands woven parallel to the longitudinal axis may prevent the device from contracting sufficiently. However, it is contemplated by the present invention that wires may be used in place of these warp strands such that the biaxially braided strands slide along these wires wherein both contraction of the device and additional longitudinal stability may still occur. If used, warp strands may only be used over a small portion of the device. Otherwise, the device's inherent ability to bend is lost. It is the inherent ability of the device to contract longitudinally that allows it to bend. A bend is achieved by contracting one side more than the other. However, unlike extruded grafts, the biaxial braid design prevents the device from collapsing.

The distance between the interlocking braided strands of fiber 8, 12 in FIG. 1 determines the degree to which the device may contract for catheter delivery. The larger this distance is, when the device is in its equilibrium or stress-free conformation (the expanded diameter), the more contraction the device can undergo until the inner diameter of the cylinder approaches zero. In the preferred embodiment, the contraction ratio to best facilitate catheter deployment is approximately five. This requires that the distance between the wires be approximately 5 times the width of the reinforcing or sealing fibers used in the braid, when the angle between the fibers is 90°. Depending upon the application, this space may make the device too porous to seal, e.g., an aneurysm or other type of vascular wall trauma subjected to arterial blood flow and the associated pressures. Typical values of the reinforcing or sealing fiber 8, 12 diameter are in the range from 0.1 to 0.5 mm. This leaves pores in the body portion 4 from 0.5 to 2.5 mm. As a consequence, layers of the braided composite material 6 are required for particular endovascular embodiments of the device. Sufficient layers may be used to reduce the porosity to an acceptable level, while each layer still possesses a contraction ratio sufficient to allow catheter delivery. If the distance between the braided strands (fibers 8, 12) in a single layer design (as shown in FIGS. 1–2) is reduced to provide a porosity sufficient to seal the device with respect to arterial blood pressure, the device will not contract sufficiently for catheter delivery.

The original angle of the reinforcing and sealing components of the composite will determine the expanded or resting diameter of the device under the equilibrium or a zero stress condition. The prosthesis of the present invention can be configured such that it can be compressed radially by applying an inward radial stress whereby these angles approach 180° near the condition of maximum compression (the radially contracted diameter), as seen in FIG. 2. This conformation is adopted when the device is mounted on a catheter (not shown) to be used for endovascular delivery of the device. A flexible tubular sheath (not shown), with very low radial compliance, comprising part of the catheter delivery system, provides the radial stress necessary to hold the device in this conformation. This stress is applied normally to the surface of the device to achieve the conformation seen in FIG. 2. Once the device is positioned in the body passage 14, e.g., a blood vessel, the sheath is removed and the graft expands to its operable diameter which is less than the expanded or resting diameter. Because the diameter of the device when deployed (the operable diameter) is less than the expanded diameter, the device exerts a radial stress normal to the inner surface of the blood vessel. It is this normal force that holds the device in place.

One embodiment of the present invention provides additional means for securing the device in place wherein the reinforcing components (fibers 8) of the composite extend along the longitudinal axis further than the sealing components (fibers 12) as shown in FIG. 3. The layer or layers of the composite material (interwoven reinforcing and sealing components) comprise the body portion 4 of the device. The extension of the stiffer reinforcing wires beyond the body portion 4 provides additional means for securing the device in the blood vessel. The expanded diameter of the end portions 18,20 of the tubular shaped member 2 may be increased somewhat over the body portion 4 of the prosthesis 10. This increase in diameter allows the reinforcing component of the device to lodge into the blood vessel wall providing additional protection against the migration of the device (as shown in FIGS. 4–5).

The deployment of the device to seal an aneurysm is seen in FIGS. 4–5. The body portion 4 of the prostheses 10 will eventually clot to seal the blood flow away from dilated blood vessel portion comprising the aneurysm 32. The prostheses is held in place by the normal force exerted on the proximal and distal ends of the aneurysm 32. The reinforcing fibers 8 that extend beyond the sealing fibers 12 of the body portion 4 assist in securing the prosthesis. The increased diameter at the end portions 18,20 of the prostheses 10 help lodge the device into the vascular wall 22.

In one embodiment, the device of the present invention may be used in the vicinity of blood vessel branches 29,31. This is accomplished by adjusting the position of the prosthesis 10 such that the branches 29,31 are covered by the segment 24 of the first end portion but not the body portion 18 as seen in FIG. 5. Blood will flow through the highly porous mesh of the segment 24, but not the body portion 4. If the aneurysm or region vascular disease completely encompasses the branching vasculature, treatment can be effected by using the bifurcated form of the device described below.

A common configuration of major blood vessels is the bifurcation. This occurs when a blood vessel splits into two separate vessels such as at the aortic bifurcation. Treatment of pathology at bifurcated areas requires that under certain conditions the composite device is fashioned as seen in FIG. 6. The main body portion 4 of this form of the prosthesis 10 consists of the interbraided, interlayered reinforcing and sealing components (fibers 8,12). As with the aforementioned description, the end portions 18,20 can consist of the braided reinforcing component (fiber 8) with a gradually increasing diameter so as to facilitate secure placement of the prosthesis 10. The bifurcation 38 can be created by either of a number of processes such as separately braiding half of the reinforcing fibers 8 in the body portion 4 of the device into separate branches (or limbs) 34,36 containing half as many reinforcing fibers 8. Such a design facilitates compression of the entire device. Although the design of the reinforcing component is such that it will contract radially in a symmetric manner, the radial contraction may become asymmetric as the device approaches its maximum contraction ratio. Therefore, the entire bifurcated prosthesis 10 can be delivered by compressing it within a single catheter sheath (not shown) for endovascular delivery. Facilitation of its correct placement may require the use of multiple sheaths. The ends of the smaller separate branches 34,36 may be compressed into smaller sheaths which may in turn be inserted into a larger sheath with the compressed main part of the body portion 4 of the bifurcated prosthesis 10.

Although the present invention has been described with reference to specific details of certain embodiments thereof, it is not intended that such details should be regarded as limitations upon the scope of the invention except as and to the extent that they are included in the accompanying claims.

What is claimed is:

1. A self-expanding intraluminal composite prosthesis, comprising: an elongated hollow tubular shaped member having a body portion, the body portion being formed by at least one layer of a composite material, the composite material being comprised of a plurality of strands of a reinforcing fiber and a plurality of strands of a sealing fiber, wherein the fibers are interwoven in a biaxially braided design thereby forming the composite material that is capable of isotropic deformation along its longitudinal axis, the hollow tubular shaped member having an expanded diameter, a radially contracted diameter, and an operable diameter which is intermediate the expanded and radially contracted diameters, the tubular shaped member being radially compressible along its longitudinal axis between the expanded and contracted diameters to permit intraluminal delivery of the tubular shaped member through a body passage to a predetermined delivery site wherein the tubular shaped member can self-expand within the body passage to its operable diameter.

2. The self-expanding intraluminal composite prosthesis of claim 1, wherein the composite material is interwoven in a biaxially braided design.

3. The self-expanding intraluminal composite prosthesis of claim 1, wherein the reinforcing fiber is comprised of a material selected from the group consisting of biocompatable metals, polymers, organic fibers and combinations thereof.

4. The self-expanding intraluminal composite prosthesis of claim 1, wherein the sealing fiber is selected from the group consisting of a biocompatable polymer and a carbon fiber.

5. The self-expanding intraluminal composite prosthesis of claim 3, wherein the polymer is selected from the group consisting of polyethyleneterepthalate, polytetrafluoroethylene, polyurethane, polysiloxane and nylon.

6. The self-expanding intraluminal composite prosthesis of claim 1, wherein the reinforcing and sealing fibers have substantially similar elastic deformation characteristics, thereby permitting isotropic deformation of the tubular shaped number.

7. The self-expanding intraluminal composite prosthesis of claim 1, wherein the tubular shaped member further comprises a first end portion and an opposing second end portion, the body portion interconnecting the end portions, and wherein at least one of the end portions has an expanded diameter that is larger than the expanded diameter of the body portion and an operable diameter, such that the larger diameter end portion exerts a force upon the luminal surface of the body passage at its operable diameter sufficient to anchor the tubular shaped member at the predetermined delivery site.

8. The self-expanding intraluminal composite prosthesis of claim 7, wherein at least one of the end portions is comprised of material selected from the group consisting of a single layer of the composite material and a single layer of the interwoven reinforcing fiber.

9. The self-expanding intraluminal composite prosthesis of claim 8, wherein the material in at least one of the end portions is interwoven in a biaxially braided design.

10. The self-expanding intraluminal composite prosthesis of claim 7, wherein the first end portion is longer than the second end portion and at least a segment of the first end portion is sufficiently porous such that placement of the segment at an intersection of a branch in the body passage allows bodily fluids to pass through the segment and into the branches of the body passage thereby maintaining fluid communication between the body passage and the branch.

11. The self-expanding intraluminal composite prosthesis of claim 1, wherein the body passage is a blood vessel.

12. The self-expanding intraluminal composite prosthesis of claim 11, wherein the blood vessel is an artery and the predetermined delivery site is an aneurysm.

13. The self-expanding intraluminal composite prosthesis of claim 1, wherein the body portion is bifurcated along a part of its length forming two branches such that the two branches have an expanded diameter that is less than the expanded diameter of the body portion proximal to the bifurcation, thereby forming a Y-shaped intraluminal prosthesis for placement in a bifurcated body passage.

14. The self-expanding intraluminal composite prosthesis of claim 1, wherein a diameter of the fibers is between about 0.1 mm and 0.5 mm.

15. The self-expanding intraluminal composite prosthesis of claim 1, wherein the layer of the composite material is porous and the pore size is between about 0.5 mm and 2.5 mm.

16. The self-expanding intraluminal composite prosthesis of claim 1, wherein a contraction ratio of the tubular shaped member is between about 3 and 10.

17. The self-expanding intraluminal composite prosthesis of claim 1, wherein the interwoven biaxially braided fibers intersect each other at a point of interlock and the angle formed by the fibers at the point of interlock is between about 60° and 130°, when the tubular shaped member is at its expanded diameter.

18. The self-expanding intraluminal composite prosthesis of claim 1, wherein the body portion comprises a plurality of layers of the composite material such that the porosity of the body portion is maintained at a predetermined level.

19. The self-expanding intraluminal composite prosthesis of claim 1, mounted on a delivery catheter within a removable sheath located on the catheter.

20. A method for treating aortic aneurysmal disease comprising delivering the device of claim 10 to the predetermined delivery site.

21. The self-expanding intraluminal composite prosthesis of claim 16, wherein the contraction ratio is about 5.

22. The self-expanding intraluminal composite prosthesis of claim 17, wherein the angle formed by the fibers at the point of interlock is about 90 degrees.

* * * * *